United States Patent
Lu

(10) Patent No.: US 6,855,350 B2
(45) Date of Patent: Feb. 15, 2005

(54) METHODS FOR INHIBITING CANCER GROWTH, REDUCING INFECTION AND PROMOTING GENERAL HEALTH WITH A FERMENTED SOY EXTRACT

(75) Inventor: Kung-Ming Lu, Taipei (TW)

(73) Assignee: Microbio Co., Ltd., Taipei (TW)

( * ) Notice: Subject to any disclaimer, the term of this patent is extended or adjusted under 35 U.S.C. 154(b) by 169 days.

(21) Appl. No.: 10/192,534

(22) Filed: Jul. 11, 2002

(65) Prior Publication Data

US 2003/0008023 A1 Jan. 9, 2003

Related U.S. Application Data

(62) Division of application No. 09/812,579, filed on Mar. 21, 2001, now abandoned.

(51) Int. Cl.[7] .......................... A61K 35/78; A61K 35/00
(52) U.S. Cl. ...................... 424/757; 424/115; 514/826
(58) Field of Search ................................ 424/757, 115; 514/826

(56) References Cited

U.S. PATENT DOCUMENTS 6,045,819 A * 4/2000 Takebe ........................ 424/442
6,303,161 B1 * 10/2001 Takebe et al. ................. 426/46

FOREIGN PATENT DOCUMENTS

JP       01095744 A    *    1/1989

OTHER PUBLICATIONS

Quak et al. Am. J. Clin. Nutr. Dec. 1998. vol. 68 (6 Suppl), MEDLINE abstract.*

* cited by examiner

Primary Examiner—Christopher R. Tate
(74) Attorney, Agent, or Firm—Rosenberg, Klein & Lee

(57) ABSTRACT

The present invention relates to the preparation of therapeutic compositions comprising of fermented soy extracts made with lactic acid bacteria and the optional addition of at least a yeast. The invention also relates to therapeutic uses of such extracts in promoting general health, improving the health of subjects, preventing and/or treating cancer, preventing infections, reducing the incidence of infections, treating infections, treating asthma, treating inflammation, modulating the immune system and treating immune disorders.

3 Claims, 7 Drawing Sheets

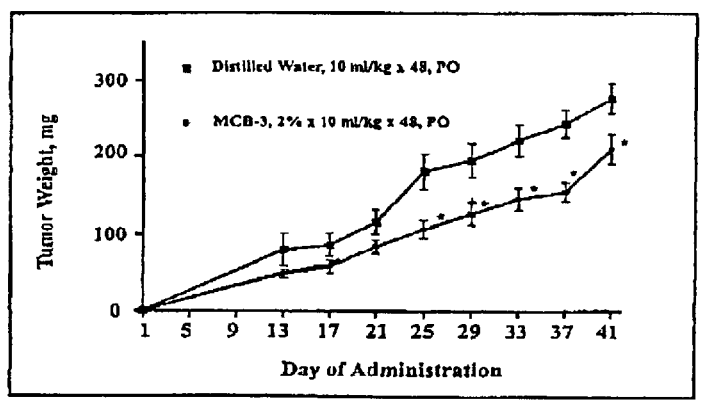
FIG. 6 The tumor growth curve of pre-administration of fermented soy extract
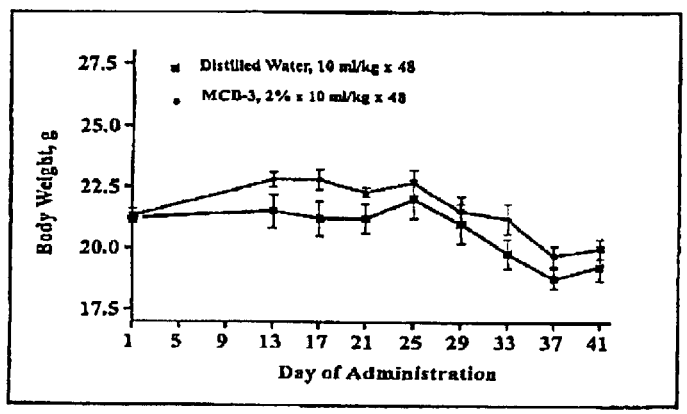
FIG. 7 The body weight curve of pre-administration of fermented soy extract

METHODS FOR INHIBITING CANCER GROWTH, REDUCING INFECTION AND PROMOTING GENERAL HEALTH WITH A FERMENTED SOY EXTRACT

CROSS-REFERENCE

This is a division of Ser. No. 09/812,579, filed Mar. 21, 2001.

BACKGROUND OF THE INVENTION

1. Field of the Invention

This invention relates to a use or method of preventing and/or treating diseases in subjects by administering a fermented soy extract, FSE, to the subjects in need of the prevention and/or treatment of the diseases. The fermented soy extract is particularly useful in preventing and/or treating cancer, preventing infections, reducing the incidence of infections, treating infections, preventing and/or treating asthma, preventing and/or treating inflammation, e.g. inflammation of the skin, modulating the immune system and treating immune disorders. The present invention also relates to methods for selectively killing tumor cells by inducing cell apoptosis, reducing cell proliferation and angiogenesis of tumor cells, and methods of inhibiting lipoxygenase, e.g. LOX-5, LOX-12 and/or LOX-15. The fermented soy extract is also useful in improving the health of subjects in need of the improvement and in promoting the health of pregnant women or infants.

2. Description of the Prior Art

Cancer chemoprevention is the use of natural or pharmaceutical agents to prevent, slow or halt the process of carcinogenesis. These agents inhibit the development of invasive cancer either by blocking the DNA damage that initiates carcinogenesis or by diverting the progression to a benign outcome, such as apoptosis or differentiation of these precancerous cells. Chemopreventive agents could be defined as: substances that reduce the synthesis of carcinogens in the body; Chemicals that enhance their detoxification by Phase I or Phase II enzymes; antioxidants that scavenge free radicals; and chemicals that trap ultimate carcinogens preventing their interaction with DNA. It is of paramount importance to ensure that chemopreventive agents must be nontoxic and relatively free of side effects, because they have to be administered over a long period of time in order to establish whether they possess efficacy in humans. For many candidate agents, mechanisms of action can be well characterized using human or other mammalian cells propagated in vitro, whereas potential toxic effects can often be predicted by administration to animals in in vivo studies. Furthermore, these agents should be taken orally, in forms of pills, foods, or beverages modified to increase the convenience and obedience of daily consumption.

Dietary epidemiological studies of cancer development have generated new clues about micronutrients and other dietary components to act as efficacious cancer preventive agents. For example, intake of soybeans and soy-based products is associated with a lower risk of several types of cancers including breast, prostate and colon cancer. Experiments in various animal models also suggested that soy consumption could decrease tumor number, incidence, latency, multiplicity and metastasis. Soybeans are the most concentrated source of isoflavones in the human diet. They also contain many other compounds including saponins, phytosterols, soy phytates, protease inhibitors, phenolic acids, complex sugars, boron, lecithin, omega-3 fatty acids and folic acid, these compounds may impart health benefits.

In general soybean-related products containing higher amount of aglycones than glucoside conjugates of isoflavones would be preferable for cancer prevention. It has been demonstrated that microbial fermentation might influence the isoflavones content and isomer distribution of soybeans and further alter the availability and metabolism in human. Glycoside conjugates may be converted to aglycones by microbes during fermentation, which also results in increasing in soluble nitrogen compounds, riboflavin, niacin, pantothenic acid, biotin, folic acids and nicotinic acid. These aglycones of isoflavones, such as genistein and daidzein, can influence steroid metabolism, inhibit protein tyrosine kinase activity, inhibit topoisomerase activity, reduce angiogenesis in vitro and in vivo, inhibit malignant cell proliferation, induce cell differentiation and stimulate apoptosis.

Apoptosis, characterized by cell shrinkage, membrane blebbing, nuclear pyknosis, chromatin condensation and genomic fragmentation, is a strictly regulated process responsible for the ordered removal of superfluous, aged and damaged cells. It does not only play an important role in the development and maintenance of tissue homeostasis but also represents an effective mechanism by which harmful cells can be eliminated. Since apoptotic programs can be manipulated to produce massive changes in cell death, the genes and proteins controlling apoptosis are potential drug target. In fact, most anticancer drugs induce apoptosis directly, thus providing less opportunity for acquired drug resistance, decreasing mutagenesis and reducing toxicity. In addition, induction of apoptosis can also serve as an excellent surrogate end-point biomarker in chemoprevention.

Many data point out that intracellular oxidative metabolites play a significant role in the regulation of apoptosis. For instance, some apoptosis-inducing agents are either oxidants or stimulators of cellular oxidative metabolisms, whereas many inhibitors of apoptosis show antioxidant activities. Indeed, factors for oxidative stress such as ROS production, lipid peroxidation, down-regulation of antioxidant defenses characterized by reduced glutathione (GSH) levels, and progressive decline in the transcript levels of superoxide dismutase (SOD), catalase and thioredoxin have been observed in some apoptotic processes. Moreover, ROS can also play an important role in apoptosis by regulating the activity of certain enzymes involved in the cell death pathway.

The association of neutropenia and infection in patients with neoplastic disorders who are receiving myelosuppressive chemotherapy was established more than three decades ago. Infection continues to be a leading cause of morbidity and mortality in such patients. The risk of infection is further enhanced by the toxicities of the cytotoxic drugs to the mucous membranes of the oral cavity and the gastrointestinal tract. Many of these infections are caused by endogenous enteric organisms. Compared with patients have profound and prolonged neutropenia (longer than 14 days), patients with short-lived neutropenia (up to 10 days) have a lower risk of developing infections and respond better to empiric antimicrobial therapy when infection does develop. Febrile neutropenic patients were hospitalized for the administration of empiric, broad-spectrum intravenous antibiotic therapy.

Various studies have shown the efficacy of protective isolation and prophylactic oral antibiotics in preventing neutropenic infections before they were admitted for empiric antibiotics. Combinations of oral, nonabsorbable antibiotics aimed at total gastrointestinal decontamination are often poorly tolerated by patients and may encourage the acquisition of resistant organisms. The alternative approach of selective gastrointestinal decontamination aims to eliminate the aerobic flora of the gut but to preserve the anaerobic flora of the gut, and hence, the colonization resistance of the host is maintained. Co-trimoxazole is a popular drug for this purpose in the past and more recently, fluoroquinolones (e.g.ciprofloxacin, ofloxacin, and levofloxacm) have been shown to be effective. However, breakthrough gram-positive infections and the emergence of resistant gram-negative bacilli are of concern with these agents.

The therapeutic and toxic effects of anti-cancer agents such as cisplatin, anthracyclines, bleomycins, alkylating agents, various cytokines and many DNA damage and apoptosis inducing agents are thought to be mediated by reactive oxygen species (ROS), including superoxide and hydroxy radicals. The symptoms general malaise, poor appetite and signs of inflammations during chemotherapy are also part of the results of free radical damage. Dietary intake of anti-oxidant, particularly the antioxidant vitamins, vitamin C and E, beta-carotene, has been associated with a diminished risk of cancers at various anatomical sites. The thiol-containing anti-oxidant, aminofostine, and lipoate are reported to decrease the chemotherapy-induced side effects. However, theoretically it is, there is no convincing evidence of clinical applicable anti-oxidants for the treatment of chemotherapy induced toxicities.

The anti-oxidant can eliminate not only the chemotherapeutic agents induced normal tissue damage but also enhance the cytotoxicity of chemotherapeutic agents in a p53-independent induction of p21 expression in cancer cell.

The toxic effects of anti-cancer agents caused by DNA damage are thought to be mediated by reactive oxygen species, the anti-oxidant can eliminate not only the chemotherapeutic agents induced normal tissue damage, but also enhance the cytotoxicity of themotherapeutic agents in a p53-independent induction of p21 expression in cancer cells.

SUMMARY OF THE INVENTION

This invention is concerned with a composition comprising a fermented soy extract, FSE. The fermented soy extract is made by fermentation of an aqueous soy bean extract with at least one lactic acid bacteria, e.g. a strain of one *Lactobacillus* species, followed by sterilization, e.g. by heat, of the fermented liquid with optional filtration and concentration. In addition to using at least one lactic acid bacteria, the fermentation of the aqueous soy extract can be conducted with at least one yeast such as a *Saccharomyces* species, e.g. *Saccharomyces cerevisiae*. The fermentation of the aqueous soy extract with one or more lactic acid bacteria and the optional yeast or yeasts can be carried out sequentially in any order or simultaneously, preferably simultaneously.

One of the aspects of the invention is a method of preventing and/or treating diseases or health disorders in a subject by administering an effective amount of the fermented soy extract to the subject in need of the prevention and/or treatment. The diseases or health disorders that can be prevented or treated with the fermented soy extract include cancer, infection, immune disorders, asthma, and inflammation, e.g. dermal inflammation. Within the scope of the invention is a method of improving the health of a subject in need of the health improvement by administering an effective amount of the fermented soy extract to the subject. The subject can be any mammal, preferably a human. The fermented soy extract improves the health of the subject by preventing cancer, treating cancer, preventing infections, treating infections, reducing the incidence of infections, modulating the immune system, preventing and/or treating immune disorders, preventing and/or treating asthma, preventing and/or treating inflammation, and/or inhibiting lipoxygenase, e.g. LOX5, LOX-12 and/or LOX-15. In addition to LOX inhibition, the fermented soy extract has anti-oxidation and/or anti-free-radical functions. The fermented soy extract can also be used to improve the health of subjects in a unique status, e.g. pregnancy or infancy, by administering an effective amount of the fermented soy extract to the subjects in a unique status.

Another aspect of this invention is a use of the fermented soy extract to prevent and/or treat diseases or health disorders in a subject in need of the prevention and/or treatment. The diseases or health disorders that the fermented soy extract is useful in be preventing and/or treating include cancer, infection, immune disorders, asthma, and inflammation, e.g. dermal inflammation. The subject can be any mammal, preferably a human. Therefore, the fermented soy extract is useful in preventing cancer, treating cancer, preventing infections, treating infections, reducing the incidence of infections, modulating the immune system, preventing and/or treating immune disorders, preventing and/or treating asthma, preventing and/or treating inflammation, and/or inhibiting lipoxygenase, e.g. LOX5, LOX-12 and/or LOX-15. Another aspect of the invention is a use of the fermented soy extract to improve the health of subjects in need of a health improvement. Also within the scope of the invention is the use of the fermented soy extract for the manufacture of a medicament for the prevention and/or treatment of diseases or health disorders, including cancer, infections, immune disorders, inflammation, and asthma. The invention also includes the use of the fermented soy extract for the manufacture of a medicament for inhibiting lipoxygenase, e.g. LOX-5, LOX-12 and/or LOX-15.

BRIEF DESCRIPTION OF THE DRAWINGS

In FIG. 1(a), curve A refers to the chemiluminescence after the addition of X and Y together; curve B refers to the chemiluminescence after the addition of Y and Z together; and curve C refers to the chemiluminescence after the addition of X and Z together. FIG. 1(b) shows that, when gallic acid was added into a mixture of X and Z at 200 seconds, the chemiluminescence was increased (i.e. the chemiluminescence occurred only in the presence of X, Y and Z all together).

FIG. 2(a) shows the chemiluminescence determined with or without acetaldehyde when EGC, i.e. epigallocatechin which is a polyphenol, was added as the antioxidant at 200 seconds. FIG. 2(b) shows that when tea was added as the antioxidant at 200 seconds, its chemiluminescence emitted in the absence of acetaldehyde (+Z) is 5.79% of that in the presence of acetaldehyde. FIG. 2(c) shows that, when vitamin C was used as the antioxidant, the chemiluminescence intensity in the absence of acetaldehyde was 64.13% of that detected in the presence of acetaldehyde.

FIG. 3(a) shows that, at a FSE concentration of 1:1, the chemiluminescence intensity in the absence of acetaldehyde was 44.13% of that in the presence of acetaldehyde. FIG. 3(b) shows that, at a FSE concentration of 1:10, the chemiluminescence intensity in the absence of acetaldehyde was 63.64% of that in the presence of acetaldehyde. FIGS. 3(c) and (d) show that, at a FSE concentration of 1:100 or 1:500, the chemiluminescence intensity in the absence of acetaldehyde was at least 90% of that in the presence of acetaldehyde.

FIG. 4(A) shows the raw data from the MTT assay and FIG. 4(B) shows the percentage of cell viability. The cell viabilities after the FSE treatments were expressed with the absorbance of the control group at each time point taken as 100% in FIG. 4(B). Each bar represents the mean (n=3) standard errors. Unpaired student t test was used to determine the significant difference (*p<0.05).

In FIG. 5(A), lane 1 represented the DNA marker; lanes 2 and 3 represented the control and FSE-treated MCF-7 cells, respectively. In FIG. 5(B), cells in the gated region were labeled with FITC-dUTP by TdT enzyme and were identified as cells that had undergone apoptosis. The result was from one experiment that is representative of three similar experiments.

FIG. 6 shows the effect of administration of the fermented soy extract (with a code name MCB-3) on the tumor weight in SCID mice implanted with MCF-7 cells in a xenograft experiment. The mean ±standard error of each of the groups are presented in FIG. 6. Unpaired Student's T-test was used to compare the treatment groups with the control (the asterisks indicate significance at p<0.05).

FIG. 7 shows the effect of administration of the fermented soy extract on the body weight of SCID mice implanted with MCF-7 cells in the xenograft experiment. The mean ±standard error of each of the groups are presented in FIG. 7. Unpaired Student's T-test was used to compare the treatment groups with the control (the asterisks indicate significance at p<0.05).

DETAILED DESCRIPTION OF THE INVENTION

Figure 1:
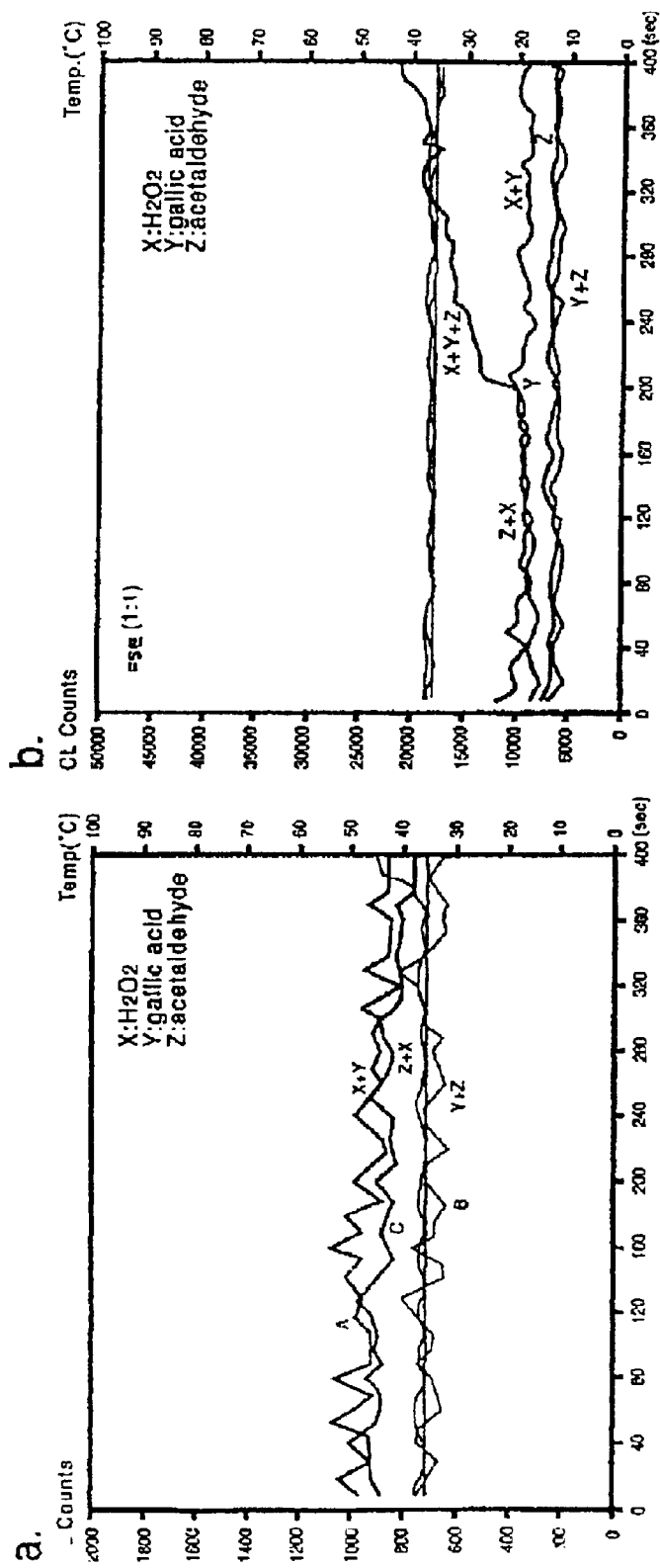
FIG. 1 shows the antioxidant effect of gallic acid. At a temperature of 37° C., chemiluminescence, CL Counts, was measured after the addition of $H_2O_2$ as a peroxide (X), gallic acid as an antioxidant (Y) and/or acetaldehyde as a radical receptor (Z).

Process for Producing the Fermented Soy Extract

The fermented soy extract is produced by fermentation of soy bean extract with at least one lactic acid bacteria, e.g. one or more strains of a *Lactobacillus* species or several strains of a number of *Lactobacillus* species, optionally together with at least one yeast, e.g. a strain of a *Saccharomyces* species. If more than one microbe is used in the fermentation, the fermentation can be conducted with the microbes sequentially or simultaneously. Preferably, an aqueous extract of non-genetically modified organic soybeans of selected grade is used as a starting material. Preferably, the fermentation is carried out using a heterogeneous culture of *Lactobacillus*, for example, a culture of 5, 10, 15, 20, 25 or 30 strains of *Lactobacillus*. More preferably, at least one yeast is added to the heterogeneous culture of *Lactobacillus*. The strains of *Lactobacillus* that can be used include, for examples, *Lactobacillus acidophilus* CCRC 10695, 14026, 14064, 14065 and/or 14079, *Lactobacillus delbrueckii bulgaricus* CCRC 10696, 14007, 14009, 14010, 14069, 14071, 14098 and/or 16054, *Lactobacillus lactis lactis* CCRC 10791, 12267, 12306, 12312, 12315, 12323, 14016, 14015 and/or 14117, *Lactobacillus kefir* CCRC 14011, and/or *Lactobacillus kefiranofaciens* CCRC 16059. The yeast that can be used include, for example, *Saccharomyces cerevisiae* CCRC 20577, 20578, 20581, 21494, 21550, 21797, 21805, 22138, 22234, 22337, 22731 and/or 22728, and/or *Candida kefyr* CCRC 21269, 21742 and/or 22057. After fermentation, the fermented liquid is sterilized, e.g. by heat or irradiation, preferably by heat, to obtain a sterilized liquid. Preferably, the sterilized liquid is filtered or centrifuged, preferably filtered, to remove most or all of the dead microbes to obtain the fermented soy extract. More preferably, the filtration step is followed by removal of some of the water from the filtrate to concentrate the fermented liquid to obtain the fermented soy extract. Unless otherwise specified, the tests performed in this application involved the fermented soy extract after the concentration step. Optionally, the fermented soy extract can be dried, e.g. via lyophilization, to obtain the fermented soy extract in a powder form.

The process can be carried out by mixing organic soybean (with fat removed) with distilled water at a ratio of 1:10. The mixture is heated at 100° C. for 30 minutes and then filtered to obtain a soy extract. Beef and kelp are boiled in distilled water for 30 minutes to obtain a broth. Salt, sugar and agar are added to produce a special agar medium. The lactic acid bacteria and yeast strains are added to the special agar medium. The lactic acid bacteria with the optional inclusion of the yeast in the medium are transferred to the soy extract and incubated at 36–43° C. for 45–50 hours. Preferably, the various strains of the microbes are grouped according to similar growth characteristics, e.g. any requirements of unique nutrient medium, whether the microbial strains could produce a good smell after fermentation and whether the grouped microbes can survive in the unique condition, so that groups of the microbes are added to the soy extract separately before the incubation. The purpose of this step is to reduce any negative interaction among the various strains. Also preferably, equal proportion of the different groups of microbial strains are added to the soy extract before the incubation and the resulting extract is incubated at 40° C. for 45–47 hours. Upon completion of the incubation period, the heterogeneous culture is then transferred to the soy extract again and incubated at 36–43° C. for 100–150 hours. The final fermented extract is heat sterilized and filtered; and 95% of the water content of the filtrate is removed in a concentrator to obtain a fermented soy extract in a concentrated or condensed form. The upper layer is then filtered through porcelain, and thereafter dispensed in containers and sealed.

A fermented soy extract was prepared as described above. The specific gravity of the fermented soy extract was 1.136 g/ml with 71.49% moisture, 5.15% ash, 0.16% crude fat, 5.45% crude protein, 0.15% crude fiber, and carbohydrate. It also contained several vitamin and minerals: vitamin B1, 0.004 mg/100 g; vitamin B2, 0.12 mg/100 g; iron, 2.17 mg/100 g; calcium, 113.55 mg/100 g and phosphorous, 379.19 mg/100 g.

Uses of the Fermented Soy Extract

In this invention, the fermented soy extract may be administered alone or in a composition comprising the fermented soy extract and a pharmaceutically acceptable carrier, diluent and/or excipient. The fermented soy extract may be administered at a dose of about 0.001 to 40 ml/kg body weight, with a maximum dose of 2000 ml per person per administration. Preferably, the dose of the fermented soy extract is 0.01 to 20 ml/kg, more preferably 0.1 to 5 ml/kg, body weight of the subject. These doses are based on the fermented soy extract in the concentrated form, but appropriate doses of the fermented soy extract in the unconcentrated form or dry powder form can be calculated accordingly. The dose can be adjusted based on the health condition of the subject or the disease to be prevented or treated.

The fermented soy extract was demonstrated to be highly safe for daily intake of 1–10 ml on a long-term basis in a 6 months chronic toxicity study of rodents. Mice receiving a dose of 10 ml/kg and 1 ml/kg for 28 days did not exhibit any significant difference or abnormal symptom in a subacute oral toxicity study. No signs of gross toxicity or mortality were observed in two groups of tested animals administered 20 ml/kg and 1 ml/kg in an acute oral toxicity study of rodents. The fermented soy extract was demonstrated to be non-mutagenic in Ames test, to not cause chromosomal damage in mammalian cells in vitro and to not induce micronuclei in bone marrow cells in ICR mice tested.

When the fermented soy extract is administered in pregnant women, the dosage of the fermented soy extract can be increased during pregnancy until the daily intake reaches 12 ml. The fermented soy extract can be administered at early and midstage pregnancy, as well as delivery. Results showed that the fermented soy extract could improve symptoms, including constipation, nausea, vomiting, and gastrointestinal discomfort, commonly found in pregnancy. In addition, the administration of the fermented soy extract can reduce abnormalities during pregnancy and at delivery. The fermented soy extract is not only good for health improvement during pregnancy, but it also produces no adverse effect as a long-term dietary supplement. Daily administration of the fermented soy extract to newborns or infants daily increases weight gain of the babies or infants. Similarly, increased weight gain can be achieved in infants of nursing mothers continuously taking the fermented soy extract.

The fermented soy extract can also enhance hemopoeitic and liver functions after a surgical operation as demonstrated through daily administration of 1 ml of the fermented soy extract along with other therapeutic products to women undergoing operation after hospital admission except for the surgery day and several post-surgery days.

Use as an Antioxidant

The fermented soy extract has prominent antioxidant and free radical scavenger activities. The fermented soy extract can remove superoxide free radicals, e.g. $O_2$—$H_2O_2$, ROO, and can act as an antioxidant for unsaturated fatty acid and fat. The fermented soy extract has a prominent ability to eliminate hyper oxygen anions to protect the cell from oxidative injury and change free radicals to harmless substances with an energy decreasing procedure.

Use as an Antimicrobial Agent to Prevent or Treat Infections

The fermented soy extract has demonstrated antimicrobial activity in vitro. It inhibits the growth of *Helicobacter pylori*, ampicillin and methycillin resistant *Staphylococcus aureus, Salmonella typhimurium, Bacillus subtilis, E.coli, Proteus vulgaris* and Vancomycin resistant *Enterococcus feacalis*. The effective concentration is generally in the range of 1–10%. The selective antimicrobial decontamination effect of fermented soy extract for prophylaxis of bacterial infection in patients who are under risk of developing neutropenia due to the concurrent treatment of anti-cancer chemotherapy is also demonstrated in 100 patients.

Use as Anti-inflammation Agent

The fermented soy extract has demonstrated anti-inflammatory effect at dosage of 10 ml/kg on the reduction of carrageenan induced hind paw edema in rats and anti-inflammatory effect on acute and chronic arthritis in adjuvant arthritis test.

The fermented soy extract is beneficial to asthmatic children. Results obtained also showed significant body weight gain in a group of children with asthma when administered with 3 ml of the fermented soy extract daily for 4 months. Blood tests showed that taking fermented soy extract can increase the RBC and Hb levels in these asthmatic children.

Use for Promoting Immune Function

In vitro study indicated that the fermented soy extract improved immune function. The effect of the fermented soy extract on modulation of the immunity of animals (Bala/c mice) was studied by treating the animal with the fermented soy extract combined with or without a challenge with various mitogens including lipopolysachrride, concanavalin A and phytohaemagglutilin. Spleen cell proliferation assay indicated that the fermented soy extract could be related with T & B cell interaction in immunity modulation. The fermented soy extract can also be correlated with anti-inflammation reaction. The soy extract also enhanced phagocytosis activity of macrophages by 71%. Similar results were found with in vivo studies in mice. It was also demonstrated that the anti-tumor effect of fermented soy extract is mediated by cytokines released. Conditioned medium from fermented soy extract-stimulated peripheral blood mononuclear cells by 45–56%. Levels of interleukin-1b, interleukin-b and tumor necrosis factor-a were much higher than those of untreated control. Since untreated Macrophages and T Lymphocytes produced little or no cytokine and normal mononuclear cells did not suppress leukemic cell growth, the anti-tumor activity is speculated to be derived from elevated level of cytokine.

Use as an Agent for Inhibiting Lipoxygenases

Studies have demonstrated that the fermented soy extract can inhibit lipoxygenases which are highly expressed in most of malignant cancer cells. The lipoxygenase that can be inhibited by the fermented soy extract includes LOX-5, LOX-12 and/or LOX-15. The inhibition of lipoxygenases by the fermented soy extract can have antiproliferative effects by modulating signal transduction, modulating growth factor activation and inhibiting oncogene expression. The inhibition of lipoxygenases by the fermented soy extract can also induce apoptosis. The induction of apoptosis by the fermented soy extract can be due to the anti-oxidant activity of the fermented soy extract. The inhibition of lipoxygenases by the fermented soy extract can also inhibit angiogenesis resulting in inhibition of membrane degradation, decreased tumor cell adhesion and motility, and inhibition of metastasis. The inhibition of lipoxygenases by the fermented soy extract can also result in anti-inflammatory activities leading so that the fermented soy extract can prevent tissue damage and modulate immune responses. With the inhibition of lipoxygenase, the fermented soy extract is useful in preventing or treating cancer, asthma, coronary heart disease, cardiac failure, inflammation, allergy, ulcerative colitis, pruritis and dermatitis, and also useful in immunomodulation.

Arachidonic acid (AA) is an essential component of the cell membrane phospholipids, and LOX is the main metabolizing enzyme in AA (Arachidonic acid) metabolism. AA metabolism can result in the generation of mutagens capable of damaging DNA and inducing mutations. AA is metabolized via two major biochemical pathways: (i) the cyclooxygenase (COX) pathway leading to the generation of prostaglandins (ii) the lipoxygenase (LOX) pathway leading the generation of hydroxy (HETEs) fatty acids. HETEs have been reported to play a significant role in cancer cell metastasis, induction of protein kinase C activity, and angiogenesis. Therefore the reduced synthesis of LOX can result in suppression of tumor growth. The fermented soy extract can be a potential LOX inhibitor. The fermented soy extract also contain genestein & other components that have been reported to inhibit LOX.

Use as Anti-cancer Agent

The fermented soy extract of the present invention has anti-cancer activity for the treatment and/or prevention of cancer, whilst overcoming one or more disadvantages of prior art chemotherapeutic agents available for the treatment cancer. The cancer that can be treated with the fermented soy extract includes the most prevalent types of cancer in the human population, namely breast cancer, colon cancer, cervix, prostate, kidney, lung, colon and liver cancers.

In cancer cells, the fermented soy extract of the present invention can induce one or more effects of inhibition of cell proliferation, induction of cell differentiation, induction of apoptosis (programmed cell death), and/or cell cycle blocking. As a consequence, the compositions of the present invention have wide ranging activity against cancer cells and are accordingly effective in the treatment and/or prevention of cancers including benign prostatic hypertrophy, prostatic cancer, breast cancer, uterine cancer, leukemia, ovarian cancer, endometrial cancer, cervical cancer, colon cancer, testicular cancer, lymphoma, rhabdosarcoma, neuroblastoma, pancreatic cancer, lung cancer, brain tumor, skin cancer, gastric cancer, oral cancer, liver cancer, laryngeal cancer, bladder cancer, thyroid cancer, liver cancer, kidney cancer and nasoharyngeal carcinoma.

Within the scope of the present invention is a fermented extract of a Chinese herb prepared in a process similar to the one described above with the substitution of the soy bean with the Chinese herb. The fermented extract of the Chinese herbs can be *Glycyrrhiza uralensis* Fish, *Lycium barbarum, Coix lacryma-jobi L* var., *ma-yune Stapf Sophora tonkinensis gapnep., Cassia btusifolia., Scutellaria baicalensis Georgi, Artemisia capillaries Thunb., Coptis chinensis Frsnch., Gentiana scabra Bge., Nelumbo nucifera Gaertn., Chrysantheiferamum morifolium Ramat., Gardenia jasminoides Ellis, Hordeum vulgare L., Cinnamomum cassia Presl, Raph, anus sativus L., Dioscorea opposita Thunb., Angelica sinensis (Oliv.), Ligusticum chuanxiong Hort., Notopterygium incisum, Paeonia lactiflora Pall., Allium satium L., Schisandra chinensis (Turcz.)* Baill, *Rehmannia glutinosa Libosch., Acanthopanax gracilistylus W. W. Smith, Equus asinus L., Ligustrum lucidum Ait., Phaseolus radiatus L., Triticum aestivum L., Dolichos lablab L., Atractylodes macrocephala Koidz., Saposhnikovia divaricata, Lonicera japonica Thund., Cinnamomum cassia Presl, Zingiber officinale Rosc., Gastrodia elata Bl., Asparagus cochinchinensis (Liur.) Merr., Dendrobiun loddigesii Rolfe.,* and *Sesamum indicum L.*

This invention will now be described with reference to the following non-limiting examples.

EXAMPLE 1

The fermented soy extract functioned as an antioxidant and in the removal of free radicals. Several models published previously were used to study the antioxidant capacity of the fermented soy extract, with Vitamin C and Trolox used as positive controls. The following methods were used for determining the antioxidant activity: (1) NBT method (2) $H_2O_2$ reduction method (3) DPPH reduction (4) TRAP reduction method (5) Conjugated diene (6) Lipid peroxidation (7) Chemiluminescence (FIG. 1, FIG. 2, FIG. 3) in the presence of active oxygen. All results demonstrated that the fermented soy extract has the highest antioxidant activity against unsaturated fatty acid and peroxidation compared with Vitamin C and Trolox.

Figure 2:
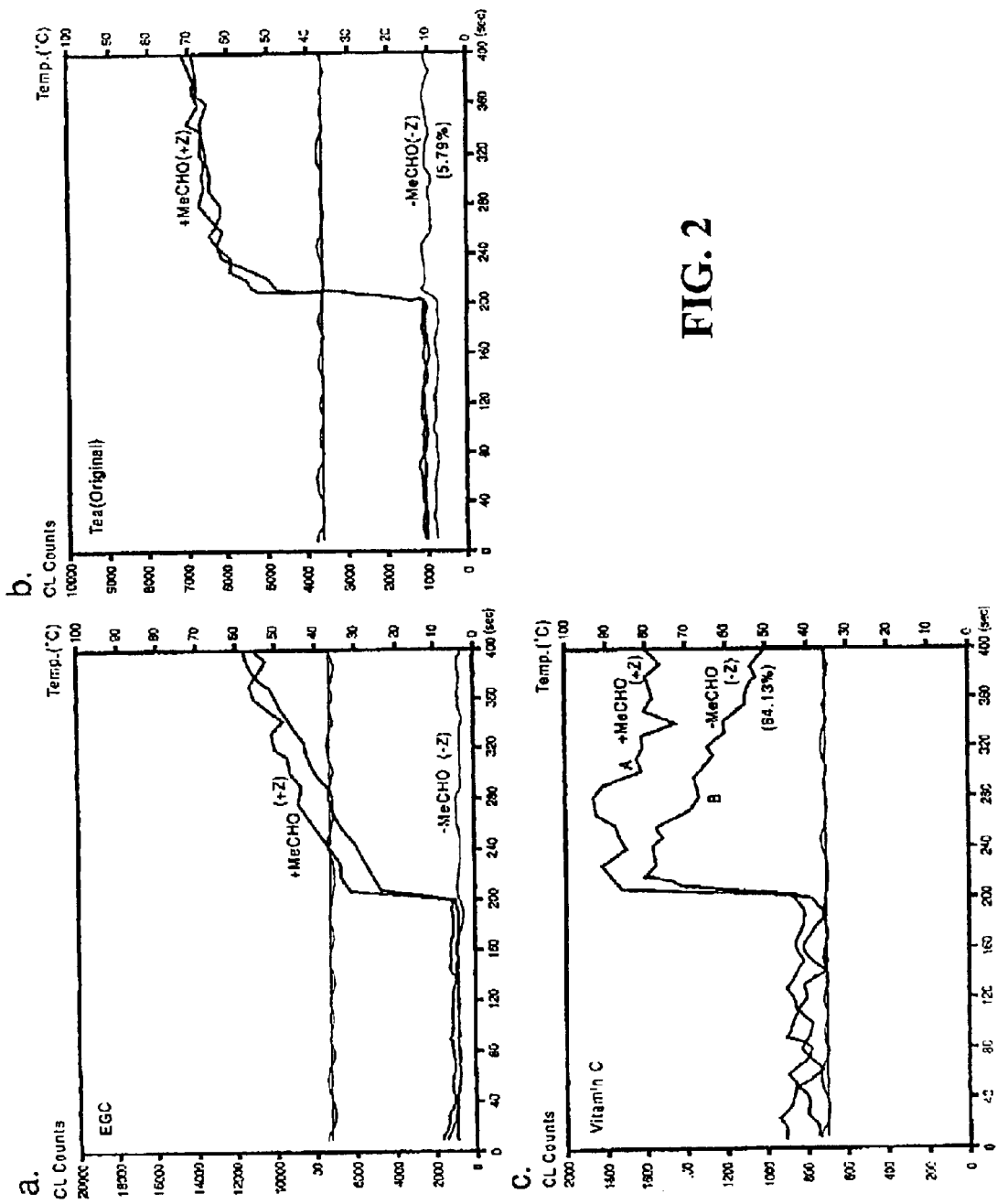
FIG. 2 shows the antioxidant effects of tea and Vitamin C At a temperature of 37° C., chemiluminescence, in CL Counts, was measured in the presence of $H_2O_2$ as a peroxide with the presence or absence acetaldehyde (Z) as a radical receptor, and an addition of one of several antioxidants, i.e. EGC, tea and vitamin C, at 200 seconds.
Figure 3:
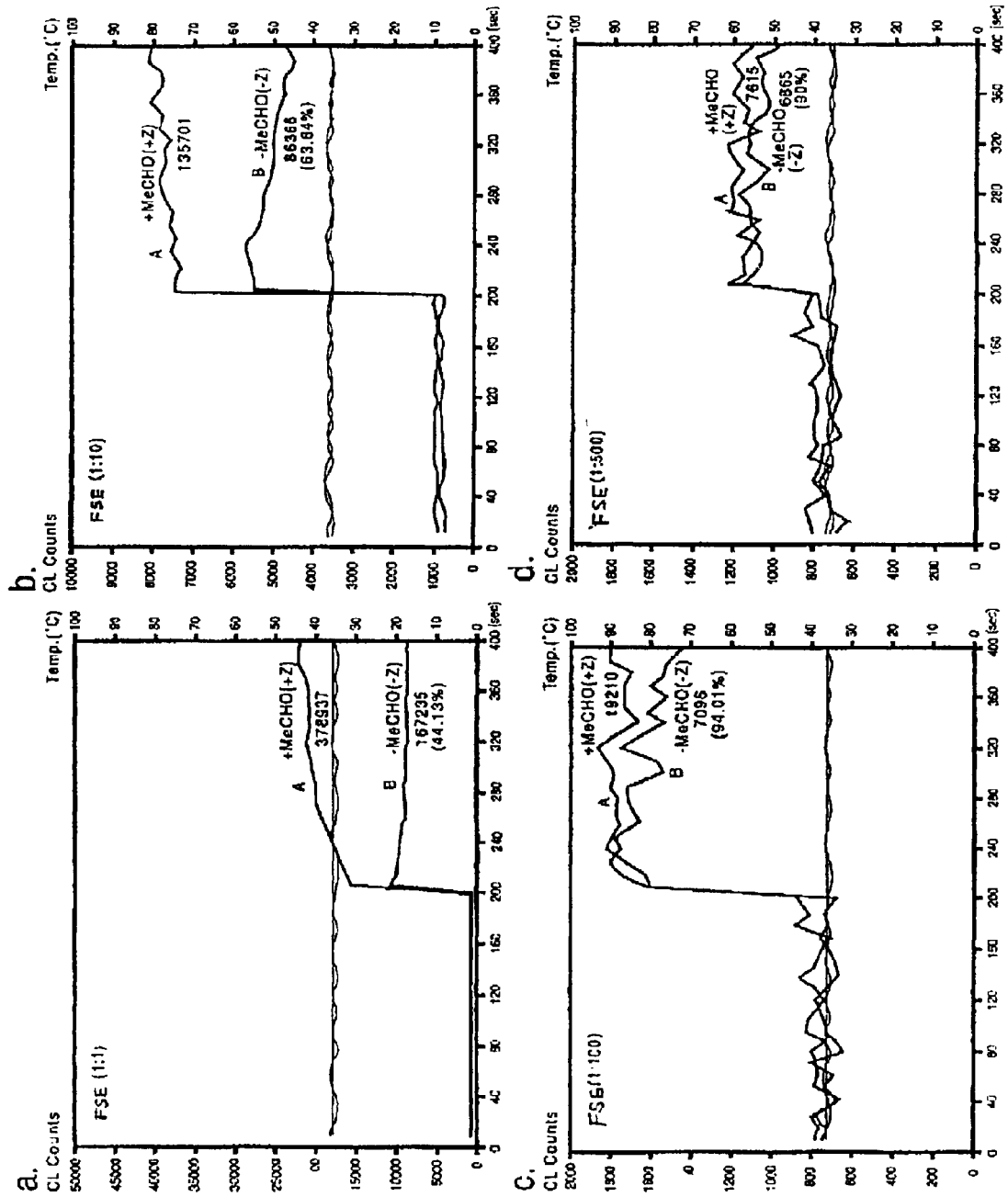
FIG. 3 shows the antioxidant effect of different concentrations of the fermented soy extract, FSE. At a temperature of 37° C., with $H_2O_2$ used as a peroxide in the presence or absence of acetaldehyde as a radical receptor (Z), the chemiluminescence was measured and the fermented soy extract at different concentrations was added at 200 seconds.

Experiments demonstrated that the fermented soy extract functions both as a antioxidant and free radical acceptor in the Okubo test system for chemiluminescence acceptor in the presence of active oxygen. The experiments were performed by measuring chemiluminescence in a liquid of hydrogen peroxide with or without acetaldehyde. Known antioxidants, e.g. gallic acid (FIG. 1 (b)), EGC, tea and vitamin C (FIGS. 2(a)–(c)) or the fermented soy extract (FIG. 3) was added at 200 seconds. The data are shown in FIGS. 1–3. FIG. 1(b) shows that chemiluminescence was increased at 200 seconds when gallic acid was added to a mixture of hydrogen peroxide and acetaldehyde. FIG. 2 shows that when EGC, tea or vitamin C was added at 200 seconds, the chemiluminescence was increased when acetaldehyde was present. However, the chemiluminescence was also increased in the absence of acetaldehyde when vitamin C was added at 200 seconds (FIG. 2(c)) demonstrating that the anti-oxidant mechanism of vitamin C probably differs from that of EGC and tea. FIG. 3 shows that, after the addition of the fermented soy extract at 200 seconds, the chemiluminescence increased indicating that the fermented soy extract was a powerful anti-oxidant. The anti-oxidant activity of the fermented soy extract means that the fermented soy extract can function in removing free radicals. With anti-oxidant and free radical removing functions, the fermented soy extract is useful in promoting the general health of individuals or improving the health of subjects in need of health improvement because oxidative stresses, such as excessive presence of reactive oxygen species and lipid peroxidation, are known to be harmful to the body.

EXAMPLE 2

Figure 4:
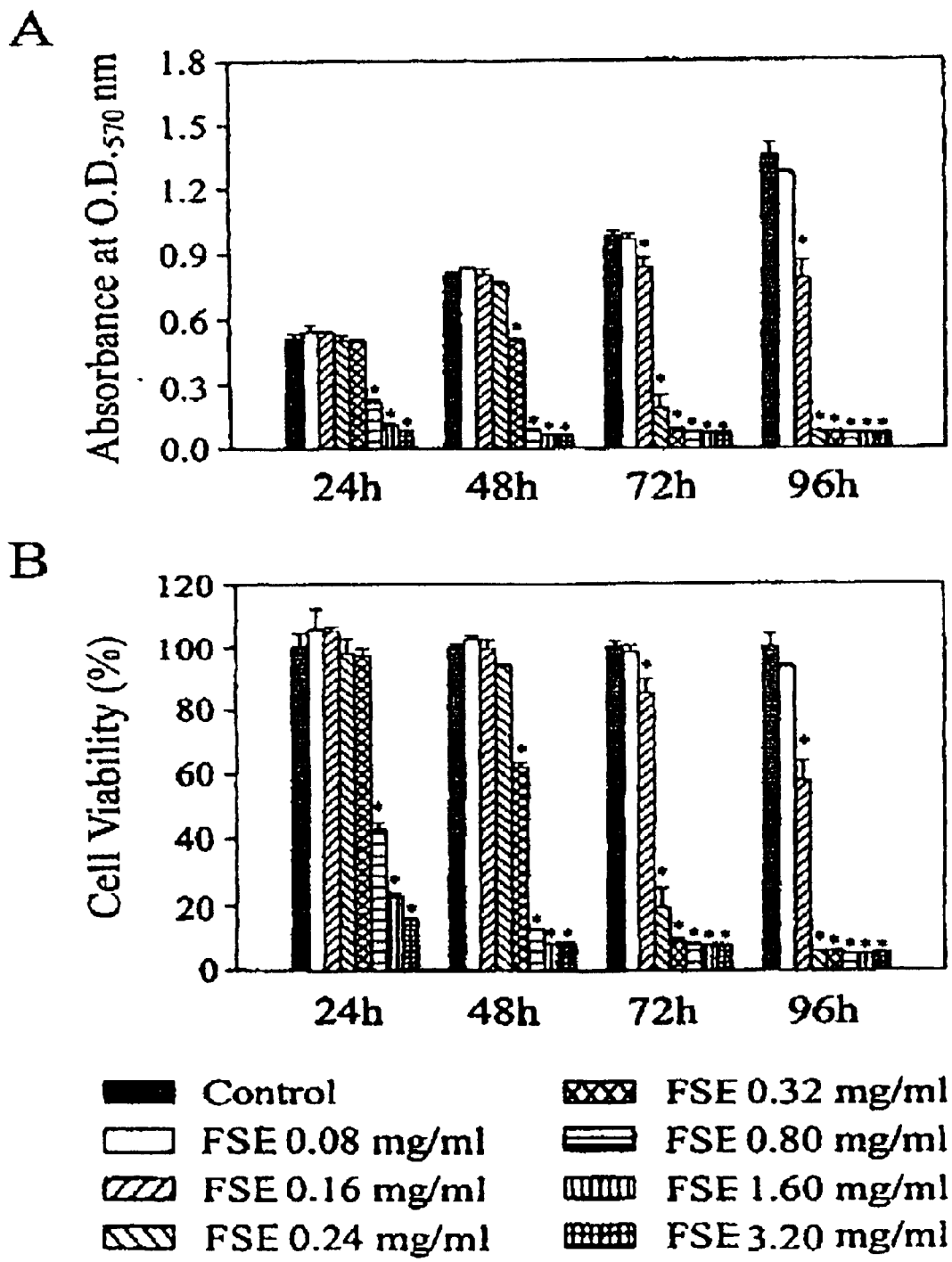
FIG. 4 shows the time course and dose response of FSE on a human breast cancer cell line, MCF-7 cells. MCF-7 cells (5 $10^4$/well) were treated with indicated doses of FSE for 24–96 hours and the viability of the MCF-7 cells was measured by an MTT assay.

A human breast cancer cell line MCF-7 (ATCC HTB-22) was used to study the anti-cancer activity of the fermented soy extract. The cytotoxic effects of the fermented soy extract was demonstrated in the cancer cell line (see FIG. 4). Compared with the control group of each cell, the value of fermented soy extract treatments was then normalized to reflect cell viability. The result showed that treatment with fermented soy extract at various concentrations (0.8 mg/ml, 1.6 mg/ml, 3.2 mg/ml, 8 mg/ml, 16 mg/ml) for 48 hours caused significant reduction in the viability of MCF-7 cells.

Experiments conducted show that strong cytotoxic activities on breast (MCF7), lung (H460) and liver (Hep G2) cell lines were detected at low (0.8 mg/ml) concentration of the fermented soy extract. Maximal cytotoxicities of cervix (HeLa) and lung (H1299) cancer cells were achieved at 3.2 mg/ml, whereas kidney (293) and colon (HT-29) cells were at 8 mg/ml. Among the cell lines tested, MCF-7 (breast cancer cell line) showed the most sensitive response.

Figure 5:
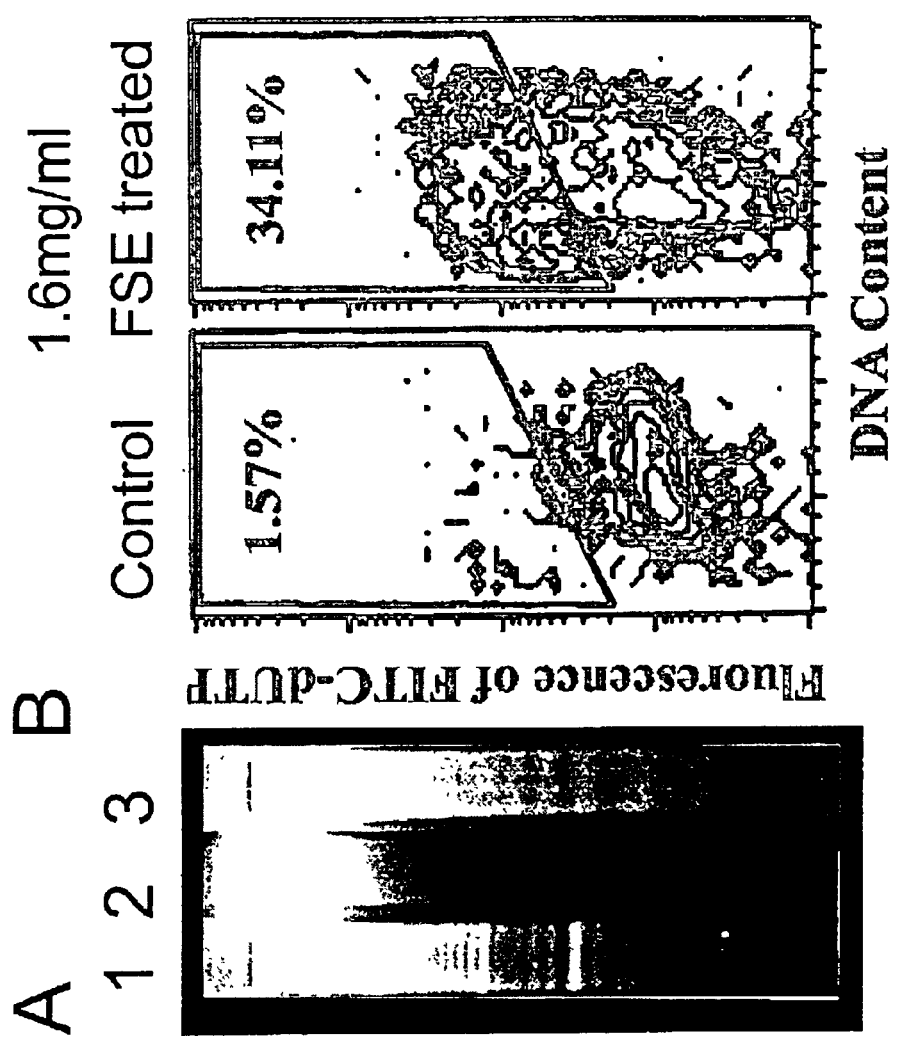
FIG. 5 shows that FSE could induce apoptotic cell death. Under a treatment of MCF-7 cells with FSE at a concentration of 1.6 mg/ml, the DNA fragmentation pattern was characterized by electrophoresis on 2.0% agarose gel and was further quantitated by TUNEL assay.

Characterized by electrophoresis as well as quantified by TUNEL assay and flow cytometry, the fermented soy extract was demonstrated to trigger apoptosis in MCF-7 cells (see FIG. 5). The apoptotic nuclei increased from 1.57% to 34.11% when the MCF-7 cells were treated with the fermented extract. The results demonstrated that the reduction of cell viability by fermented soy extract was cause by a successfully triggering of apoptotic cell death, at least, in the case of MCF-7 cells.

EXAMPLE 3

The fermented soy extract was diluted with distilled water to make a 2% solution. Severe combined immune deficiency (SCID) female mice were transplanted with MCF-7 cells via a subcutaneous injection of $1 \times 10^7$ MCF-7 cells into the dorsal side of the mouse (this day was denoted as day 1). Estradiol benzoate was injected subcutaneously weekly at a dose of 50 ug/mouse for 4 weeks. The SCID mice were administered daily with a carrier or 2% fermented soy extract by oral gavage in a dosing volume of 10 ml/kg body weight for 7 days before tumor cells implantation and then daily for 41 days after tumor cells implantation (the dose of 10 ml of the 2% solution per kg body weight was equivalent to a dose of 0.2 ml of the fermented soy extract in the concentrated form per kg body weight). The tumor size, body weight, and the signs of overt animal toxicity after fermented soy extract treatment were observed and recorded. According to the results obtained (see FIG. 6), the fermented soy extract significantly inhibit the tumor growth from day 25 to day 41. Body weight of the tested animals did not have significant difference compared with the control group (see FIG. 7). No signs of overt animal toxicities were seen throughout the experiment. Daily oral intake of the fermented soy extract was considered to have anti-tumor effects.

EXAMPLE 4

The anti-microbial acitivities of the fermented soy extract were demonstrated by determining with in vitro methods. In the first experiment, *Salmonella typhimurium*, *Bacillus subtilis*, three strains (TMU-C74, TMU-D 16 and TMU-E86) of *Helicobacter pylori* and vancomycin resistant *Enterococcus feacalis* were cultured in nutrient broth or BHI broth and transferred to Mueller Hinton agar plates or chocolate agar plates. The fermented soy extract was put on a paper disk on the agar plate and the size of an inhibition zone was measured after incubation at 37° C. The data are shown in the table below.

| Microbe Zone (mm) | Fermented Soy Extract | Inhibition |
|---|---|---|
| *Salmonella typhimurium* | Undiluted | 11 |
| *Bacillus subtilis* | Undiluted | 14 |
| *H. pylori* TMU-C74 | Undiluted | 15 |
| *H. pylori* TMU-D16 | Undiluted | 16 |
| *H. pylori* TMU-E86 | Undiluted | 15 |
| V. R. *E. feacalis* | Undiluted | 25 |
| V. R. *E. feacalis* | Diluted 50% | 15 |

In another experiment, the minimal inibitory concentrations (MICs) of the fermented soy extract were determined in *Salmonella typhimurium* (ATCC 14028), *Bacillus subtilis* (CRCC 10447), *Staphylococcus aureus* (ATCC 25923) and vancomycin resistant *Enterococcus feacalis*. Suspensions of these bacteria were adjusted to $3 \times 10^5$ CFU/ml. The adjusted bacteria suspensions were added to a 96-well plate with or without various concentrations, i.e. 10%, 5%, 2.5%, 1.25%, 0.65%, or 0.32%, of the fermented soy extract. The plate was incubated at 37° C. for 15 hours. The MICs were determined after incubation and shown in the table below.

| Microbe | MIC of Fermented Soy Extract |
|---|---|
| *Salmonella typhimurium* | 2.5% |
| *Bacillus subtilis* | 2.5% |
| *Staphylococcus aureus* | 2.5% |
| V. R. *Enterococcus feacalis* | 1.25% |

EXAMPLE 5

The effects of the fermented soy extract on immunity modulation were studied.

(A) In vitro studies:

Spleen Cell Proliferation Assay (MTT Method).

Spleen cells were isolated from mice and put in a culture flask at $2 \times 10^6$ cells/ml in a RPMI medium with or without one of several mitogens, i.e. lipopolysaccharide (LPS), concavalin A (Con A) and phytohemagglutinin (PHA). The spleen cell cultures were incubated overnight for MTT assay.

A sub-optimal concentration of 5 ug/ml of LPS combined with the fermented soy extract at 1%, 0.5%, 0.1%, 0.05% or 0.01%, had no effect on spleen cell proliferation, especially for B cells. A concentration of 5 ug/ml of PHA combined with 0.05% of the fermented soy extract increased the spleen cell number, especially for T cells, which was 2.32 fold of the spleen cell number obtained with PHA alone. According to this result, the fermented soy extract has an effect on T and B cell interaction in immunity modulation. A concentration of 5 ug/ml of Con A combined with 0.05% of the fermented soy extract produced a spleen cell number which was about 20% less than the spleen cell number obtained with Con A alone. According to this result, the fermented soy extract could play a role in anti-inflammation reactions.

Macrophage Activity Assay.

Balb/c mice were injected with thiogllate. Three to four days after the injection, macrophages were isolated from the peritoneal cavity of the mouse and incubated with or without the fermented soy extract at 37° C. for 30 minutes. *E. coli* cells conjugated with a fluorescence probe were added to the macrophage suspension and incubated at 37° C. for 2 hours. A phagocytosis assay was conducted with flow cytometry. The data showed that the fermented soy extract at 0.05% enhanced the phagocytosis activity of the macrophage by about 71% compared with macrophages not treated with the fermented soy extract.

(B) In vivo studies

Male ICR albino mice were injected intraperitoneally with vehicle, 0.8 ml of 1% of the fermented soy extract per mouse, 0.8 ml of 0.1% of the fermented soy extract per mouse, Levamisole at 30 mg/kg, or azimexone at 100 mg/kg. One hour after the intraperitoneal injection, *Candida albican* (ATCC 10231) was injected intravenously into the mouse at 1.5 to $2 \times 10^7$ CFU per mouse. The mortality of the mouse was determined daily for 10 days (see Table 1). As shown in Table 1, the fermented soy extract reduced the mortality of *Candida albican* in the mouse. The mortality reductive effect of the fermented soy extract was more pronounced than that of levamisole.

Male ICR albino mice were pretreated with cyclophosphamide at 30 mg/kg on days 5, 3 and 1 before injected intravenously with *Candida albican*. On days 6, 4 and 2 before the intravenous injection of *Candida albican*, the mouse was treated with vehicle, 0.1% of the fermented soy extract, 1% of the fermented soy extract or azimexone at 100 mg/kg. The mortality of the mouse was determined daily for 10 days (see Table 2). As shown in Table 2, with cyclophosphamide pretreatment, the fermented soy extract reduced the mortality of *Candida albican* in the mouse. The mortality reductive effect of the fermented soy extract was comparable to that of azimexone.

EXAMPLE 6

Figure 8:
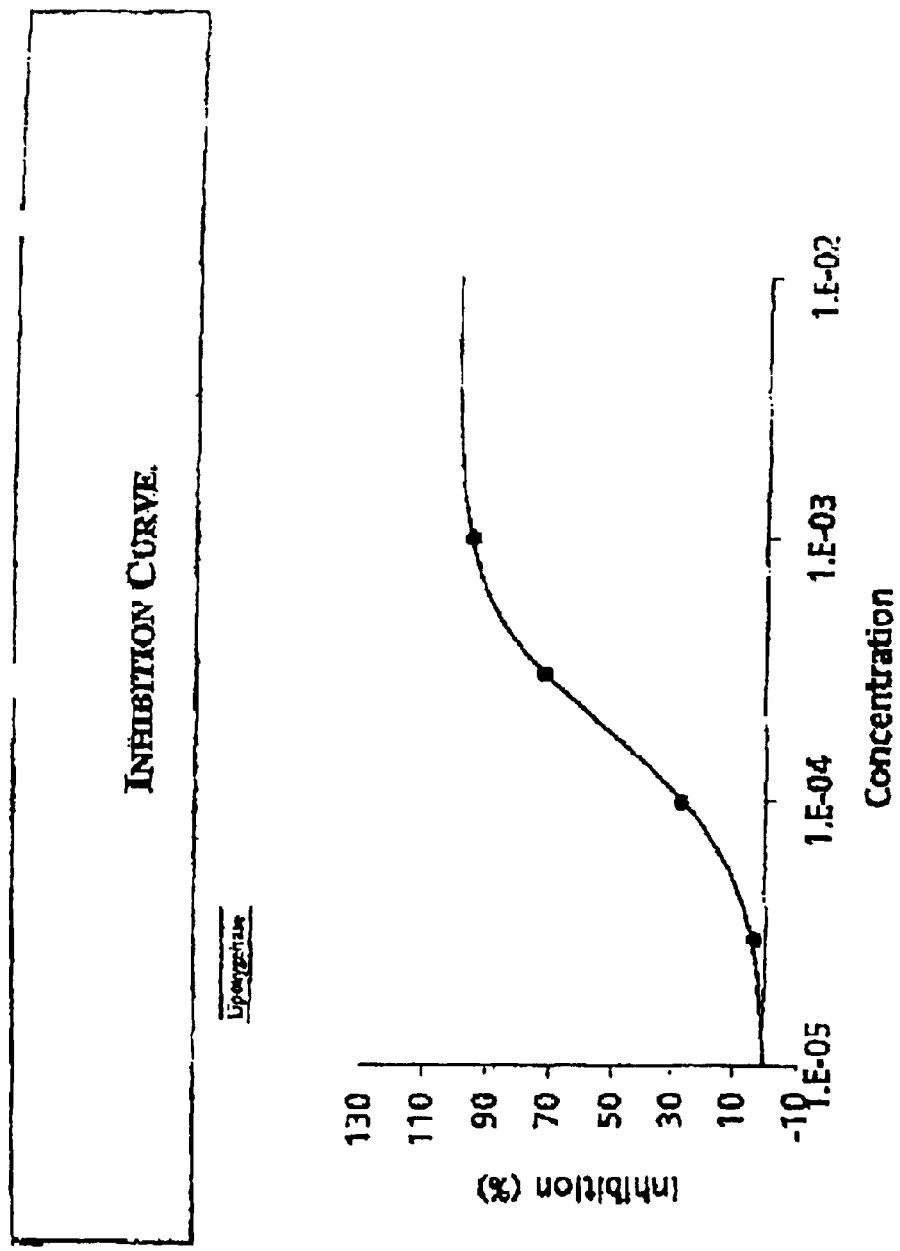
FIG. 8 shows the inhibition of LOX-15 with the fermented soy extract.

LOX is the main metabolizing enzyme in arachidonate acid (AA) metabolism. One of the metabolic pathways of AA involves lipoxygenase, LOX, which leads to the formation of HETE (hydroxyeicosatetraenoic acid). HETE has been reported to play an important role in cancer cell metastasis. HETE can induce protein kinase C activity to result in cancer cell metastasis. HETE is also a mitogenic factor, which results in angiogenesis of cancer cells. LOX-15 was isolated from rabbit reficulocytes. Linoleic acid was used as a substrate of LOX-15 with or without the fermented soy extract. The amount of HETE formed was determined spectrophotometrically. The data show that the fermented soy extract had an inhibitory effect on LOX-15 (see FIG. 8). The result indicated that the fermented soy extract can inhibit angiogenesis and metastasis of cancer cells and induce apoptosis of cancer cells.

REFERENCES

Adlercreuz, H. et al., Evaluation nutrition, intestinal microflora and prevention of cancer: a hypothesis, Proc. Soc. Exp. Biol. Med., 217:241–246 (1998).

Breimer L H. Ionizing radiation-induced mutagenesis, Br J Cancer, 57:6–18 (1998).

Briehl, M. M. et al., Modulation of the antioxidant defense as a factor in apoptosis, Cell Death Differ., 3:63–70 (1996)

Chemoprevention Working Group to the American Association for Cancer Research, Cancer Res. 59:4743–4758 (1999).

Cohen, L. A. et al., Effect of intact and isoflavone-depleted soy protein on NMU-induced rat mammary tumorigenesis, Carcinogenesis, 2: 929–935 (2000).

Dwyer, J. T. et al., Tofu and soy drinks contains phytoestrogenes, J. Am. Diet Assoc., 94: 739–743 (1994).

Ghibelli, L. et al., Rescue of cells from apoptosis by inhibition of active GSH extrusion, FASEB J., 12:479–486 (1998).

Greenwald, P. et al., Chemoprevention, CA-Cancer J. Clin., 45:31–49 (1995).

Hong, W. K. et al., Recent advances in chemoprevention of cancers, Science, 278:1073–1077 (1993).

Hutchins, A. M. et al., Urinary isoflavoneoid phytoestrogen and lignan excretion after consumption of fermented and unfermented soy products, J. Am. Diet Assoc., 95:545–551 (1995).

Ikeda, Y. et al., The molecular basis of brain injury and brain edema: the role of oxygen free radicals, Neurosurgery, 27:1–11 (1990).

Keisari, Y. et al., A simple calorimetric method for the measurement of hydrogen peroxide produced by cells in culture, J. Immunol Methods., 38:161–170 (1980).

Kelloff, G. J., Approaches to the development and marketing approval of drugs that prevent cancer, Cancer Epidermiol. Biomarkers Pre., 4:1–10 (1995).

Kontos H A et al., Oxygen radicals in brain injury, CNS Trauma, 3:257–63 (1986).

Messina, M. et al., Soy intake and cancer risk: a review of the in vitro and in vivo data, Nutr. Cancer, 21:113–131 (1994).

Nout, M. J. R. et al., Recent development in temphe research, J. Appl. Bacteriol., 69:609–633 (1990).

Plamer, H. J. et al., Reactive oxygen species and antioxidants in signal transduction and gene expression, Nutr. Rev, 55: 353–361 (1997).

Robak J. et al., Flavonoids are scavengers of superoxide anions, Biochemical Pharmacology, 37(5):837–41 (1988).

Shao, Z. M. et al., Genistein exerts mutiple suppressive effects on human breast carcimona cells, Cancer Res., 58:4851–4857 (1998).

Steinberg D. et al, Beyond cholesterol: modifications of low-density lipoprotein that increase its atherogenicity, N Engl J Med, 320:915–24 (1989).

Toshiki, Y. et al., Mechanism of catechin chemiluminescence in the presence of active oxygen, J. Biolumin. Chemilumin., 11:131–136 (1996).

Wang, H. et al., Isoflavone content of commercial soybeans foods, J. Agric. Food Chem., 42:1666–1673 (1994).

I claim:

1. A method for treating and/or reducing a risk of asthma and asthmatic attacks in a human subject, comprising the steps of:

(a) fermenting an aqueous soy extract with at least one lactic acid bacteria together with at least one yeast to form a fermented liquid;

(b) sterilizing said fermented liquid;

(c) filtering said sterilized fermented liquid;

(d) removing water from said filtered fermented liquid to form a concentrated fermented soy extract liquid; and (e) administering to the human subject a predetermined amount of said concentrated fermented soy extract liquid effective to inhibit lipoxygenase.

2. The method of claim 1, wherein the lipoxygenase is LOX-5, LOX-12, and/or LOX-15.

3. The method of claim 1, wherein the lactic acid bacteria is a *Lactobacillus* species and the yeast is a *Saccharomyces* species.

* * * * *